(12) United States Patent
Lee et al.

(10) Patent No.: US 10,151,757 B2
(45) Date of Patent: Dec. 11, 2018

(54) ACHROMATIC COLORIMETRIC SENSOR USING NANO PARTICLES

(71) Applicant: RESEARCH & BUSINESS FOUNDATION SUNGKYUNKWAN UNIVERSITY, Suwon-si (KR)

(72) Inventors: Jung Heon Lee, Seoul (KR); Jun Hyuk Heo, Suwon-si (KR); Seok Young Yoon, Busan (KR); Gyu Sung Yi, Suwon-si (KR); Byoung Sang Lee, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 71 days.

(21) Appl. No.: 15/234,393

(22) Filed: Aug. 11, 2016

(65) Prior Publication Data
US 2017/0045523 A1    Feb. 16, 2017

(30) Foreign Application Priority Data

Aug. 11, 2015 (KR) ......... 10-2015-0113393
May 11, 2016 (KR) ......... 10-2016-0057708

(51) Int. Cl.
*G01N 33/58* (2006.01)
*G01N 21/78* (2006.01)
*G01N 21/552* (2014.01)

(52) U.S. Cl.
CPC ......... *G01N 33/587* (2013.01); *G01N 21/554* (2013.01); *G01N 21/78* (2013.01)

(58) Field of Classification Search
None
See application file for complete search history.

(56) References Cited

U.S. PATENT DOCUMENTS 6,361,944 B1 * 3/2002 Mirkin ............. B82Y 5/00
                                                    435/6.11
2015/0038361 A1 * 2/2015 Erickson ......... G01N 33/5088
                                                    506/9

FOREIGN PATENT DOCUMENTS

KR    10-1502277 B1    3/2015
WO    WO-2013123178 A1 * 8/2013 ......... G01N 33/5088

OTHER PUBLICATIONS

Kim, Ji-Young, et al. "Multiplexed DNA Detection With DNA-Functioned Silver and Silver/Gold Nanoparticles Superstructure Probes." *Bulletin of the Korean Chemical Society* 33.1 (2012): 221-226. (6 pages in English).

* cited by examiner

Primary Examiner — Betty J Forman
(74) Attorney, Agent, or Firm — NSIP Law

(57) ABSTRACT

The present disclosure provides an achromatic colorimetric nanosensor, by using a mixture of nanoparticles with complementary colors. The color changes from an achromatic color to a chromatic color enables more clear color-transition and, thus, allows immediate analysis of the presence of a target analyte. Further, the present disclosure provides achromatic colorimetric nanosensor for detection of multiple analytes using plural nanoparticles via color changes from an achromatic to multiple chromatic colors.

10 Claims, 11 Drawing Sheets

Specification includes a Sequence Listing.

FIG. 1A
Conventional
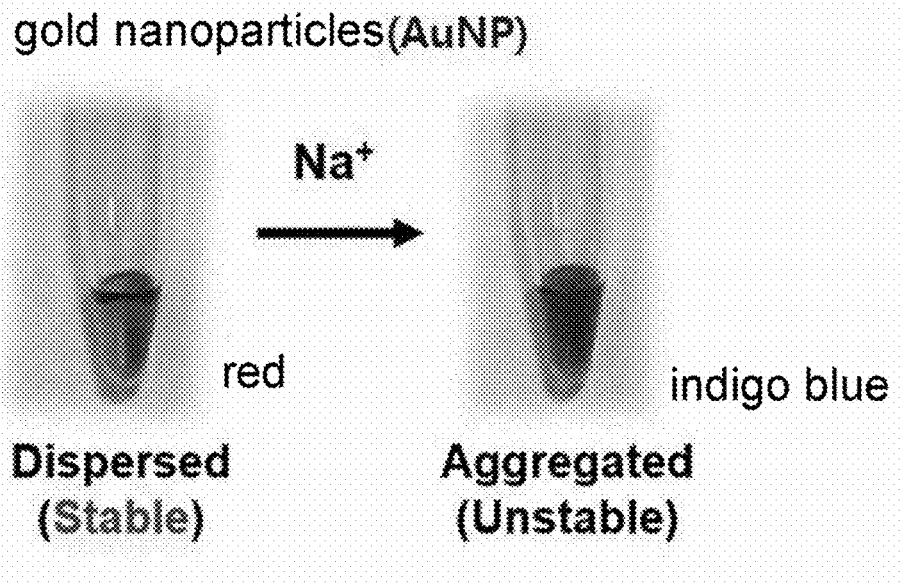
FIG. 1B
Conventional
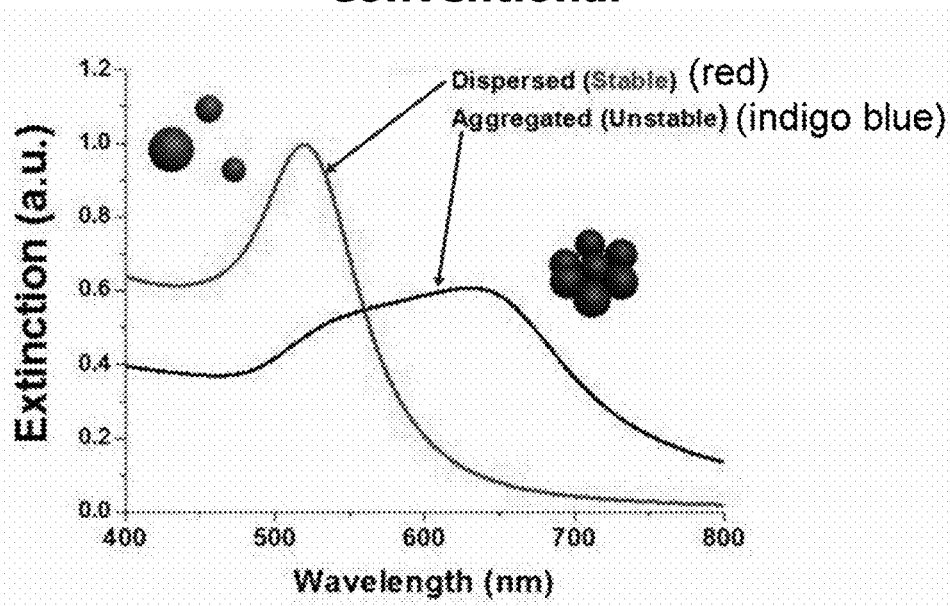

1. Using AuNS-DNA1 in 1XPBS
2. Using AuNS-DNA2 in 1XPBS
3. Using AuNS-DNA1 + AuNS-DNA2 (Complementary) in 1XPBS
4. Using AuNS-DNA1 + AuNS-DNA2 in 1XPBS (after heating)

SEQUENCE LISTING

<160> NUMBER OF SEQ ID NOS: 2

<210> SEQ ID NO 1
<211> LENGTH: 15
<212> TYPE: DNA
<213> ORGANISM: Artificial Sequence
<220> FEATURE:
<223> OTHER INFORMATION: synthesized

<400> SEQUENCE: 1
ggttggtgtg gttgg                                        15

<210> SEQ ID NO 2
<211> LENGTH: 15
<212> TYPE: DNA
<213> ORGANISM: Artificial Sequence
<220> FEATURE:
<223> OTHER INFORMATION: synthesized

<400> SEQUENCE: 2
ccaaccacac caacc                                        15

ACHROMATIC COLORIMETRIC SENSOR USING NANO PARTICLES

CROSS-REFERENCE TO RELATED APPLICATION

This application claims the benefit under 35 USC 119(a) of Korea Patent Application No. 10-2015-0113393 filed on Aug. 11, 2015 and 10-2016-0057708 filed on May 11, 2016, the entire disclosures of which are incorporated herein by reference for all purposes.

BACKGROUND

1. Field

The following description relates to an achromatic colorimetric sensor using nanoparticles, and, more particularly, to a colorimetric nanosensor which contains a mixture of complementary colored metallic nanoparticles.

2. Discussion of Related Art

A metallic nanoparticle exhibits a specific color due to a strong surface plasmon absorption. When the metallic nanoparticles are exposed to and react with an analyte, the specific color thereof may be changed to a different color. This color change of metallic nanoparticles can be observed with human naked eye. For this reason, the metallic nanoparticles may be employed as bio-analytic sensors, biological sensors or chemical sensors.

However, color changes of most nanoparticle based colorimetric sensors may occur from a chromatic color to another chromatic color. Thus, the color change may not be easily noticeable due to a small difference in terms of contrast and brightness. Thus, the reaction condition and/or reacted analyte may be poorly identified with conventional colorimetric nanosensors whose color changes occur between chromatic colors.

Thus, due to the small color changes in terms of contrast and brightness occurring in the conventional colorimetric nanosensor system, an immediate determination of the color change may be limited. Furthermore, as a color change generally occurs from one color to another from a certain type of nanoparticle, it is difficult to use conventional colorimetric nanosensor system for multiplexed detection of various analytes.

FIG. 1A and FIG. 1B show an example of a conventional colorimetric nanosensor using metallic nanoparticles. In the conventional colorimetric nanosensor, gold nanoparticles in a dispersed state exhibit red color. When the gold nanoparticles react with an analyte, gold nanoparticles may aggregate and their color will turn into an indigo blue color. Furthermore, as the color change of gold nanoparticle occur from red to indigo blue, it is difficult to use conventional colorimetric nanosensor with gold nanoparticles for multiplexed detection of various analytes.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

The following description provides a solution to overcome the problem of conventional colorimetric nanosensors, whose color changes occurring between chromatic colors limits immediate determination with naked eye due to small color differences in terms of contrast and brightness.

To this end, the following description provides an achromatic colorimetric nanosensor, by using a mixture of nanoparticles with complementary colors. The color change from an achromatic color to a chromatic color enables more clear color-transition and, thus, immediate analysis of the presence of a target analyte.

Further, the present disclosure provides an achromatic colorimetric nanosensor for detection of multiple analytes using plural nanoparticles via color changes from an achromatic to multiple chromatic colors. The sensor composed of complementary colored nanoparticles will initially have achromatic color but will turn to a chromatic color in the presence of an analyte.

Further, the achromatic colorimetric nanosensor for detection of multiple analytes may be composed of a mixture of plural complementary colored nanoparticles based on a subtractive mixing method to render an achromatic color.

In one general aspect, an achromatic colorimetric sensor includes the first nanoparticles with color change in reaction with an analyte, wherein the first nanoparticles are metallic, wherein the first nanoparticles render a first color before the color change; and the second or additional nanoparticles mixed with the first nanoparticles, wherein the second or additional nanoparticles collectively render a second color, wherein the second color is complementary to the first color.

In an embodiment, the second or additional nanoparticles may be metallic.

In an embodiment, the second or additional nanoparticles may have amphiphilic polymers coated thereon.

In an embodiment, the color change of the colorimetric sensor may include a change from an achromatic color to a chromatic color.

In an embodiment, the first nanoparticles may have chemical or biological molecules coated thereon, wherein the chemical or biological molecules may be active.

In an embodiment, the chemical or biological molecules may be selected from a group consisting of DNA, RNA, aptamer, peptide, protein, antigen, antibody, chelator, etc.

In an embodiment, the achromatic colorimetric sensor may include a chemical sensor, a biological sensor, or a biomolecule sensor.

In another general aspect, an achromatic colorimetric sensor for multiplexed detection includes a mixture of at least two nanoparticles based on a subtractive mixing method to allow the mixture to render an achromatic color; and a chemical or biological molecule attached to each of the at least two nanoparticles, wherein when a corresponding chemical or biological molecule reacts with a corresponding analyte, the mixture has a color change.

In an embodiment, reactions of the chemical or biological molecules attached to at least two nanoparticles may enable at least three color changes of the achromatic colorimetric sensor.

In an embodiment, the color change of the mixture may include a color change from an achromatic color to a chromatic color.

In an embodiment, the analyte sensor may include a chemical sensor, a biological sensor, or a biomolecule sensor.

In an embodiment, the chemical or biological molecule may have an activity.

In an embodiment, the chemical or biological molecule may be selected from a group consisting of DNA, RNA, aptamer, peptide, protein, antigen, antibody, chelator, etc.

In accordance with the following description, the achromatic colorimetric sensor may allow the color change from an achromatic color to a chromatic color. The color change from an achromatic color to a chromatic color may enable more clear color-transition and, thus, immediate analysis of the presence of a target analyte with naked eye.

Further, the achromatic colorimetric nanosensor may initially exhibit an achromatic color, by mixing plural complementary colored nanoparticles, but turns to multiple chromatic colors in the presence of analytes. Thus, the metallic nanoparticle-based achromatic colorimetric nanosensor may be able to detect various analytes concurrently. Due to the color change occurring from an achromatic color to multiple chromatic colors with enhanced changes in color contrast and brightness, the immediate analysis of the multiple targets with naked eye may be realized. This may lead to establishment of a novel multiplexed detection sensing platform.

Other features and aspects will be apparent from the following detailed description, the drawings, and the claims.

BRIEF DESCRIPTION OF THE DRAWINGS

FIG. 1A and FIG. 1B show a conventional colorimetric nanosensor using metallic nanoparticles.

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTIONS

Figure 2A:
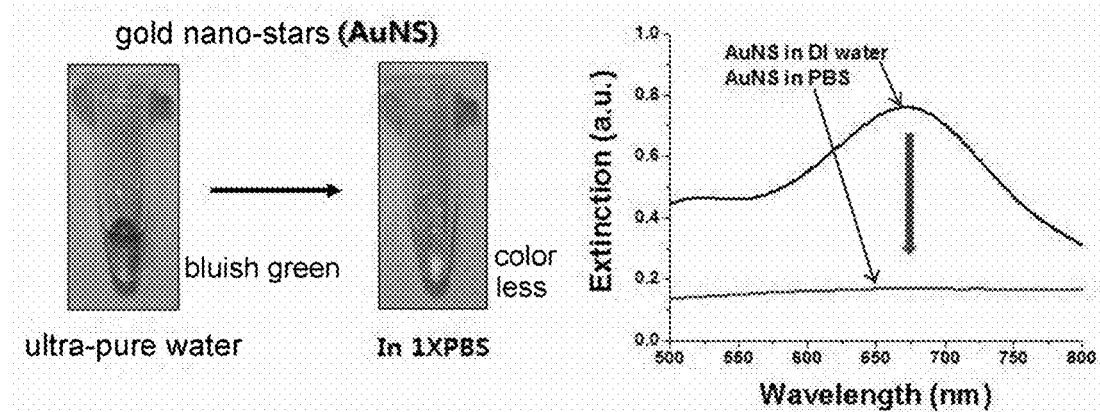
FIG. 2A shows the color-transition and change of UV-vis spectrum when gold nano-stars (AuNS) are used as metallic nanoparticles.

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

The terminology used herein is for describing various examples only, and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

The features of the examples described herein may be combined in various ways as will be apparent after an understanding of the disclosure of this application. Further, although the examples described herein have a variety of configurations, other configurations are possible as will be apparent after an understanding of the disclosure of this application.

Further, the use of "may" when describing embodiments of the present disclosure refers to "one or more embodiments of the present disclosure."

Hereinafter, embodiments of the present disclosure will be described in details with reference to attached drawings.

As used herein, a term "nanoparticles" may refer to one to three dimensional nano-particles such as nano-stars, nano-particles, nano-rods, etc. As used herein, a term "nanoparticles" may include metallic nanoparticles, dye particles, etc.

As used herein, a term "subtractive mixing" may refer to a color mixing method where a color of a resultant mixture has a lower brightness than those of original colors. Especially, the subtractive mixing may be employed to render an achromatic color.

The metallic nanoparticles may be rendered to have a specific color due to strong surface plasmon absorption. When the metallic nanoparticles are exposed to and react with an analyte, the specific color of nanoparticles thereof may be changed to a different color once perceived to the human naked eye.

The present applicants allow an achromatic colorimetric sensor using nanoparticles which changes its color from an achromatic color to a chromatic color when exposed to an analyte. This may lead to clearer identification of color-transition and thus easy detection of a target analyte.

Further, in the present disclosure, achromatic colorimetric nanosensor rendering an achromatic black color can be produced by using a subtractive mixing method based on a RYB (Red-Yellow-Blue) color model. The achromatic colorimetric nanosensor may have multiplexed detection functionality when its black color changes into multiple different chromatic colors in the presence of multiple analytes.

Hereinafter, an achromatic colorimetric sensor using nanoparticles is first described, and, then, an achromatic colorimetric sensor system with multiplexed detection functionality using nanoparticles is described in details.

In an embodiment, an achromatic colorimetric sensor using nanoparticles may include the first metallic nanoparticles with color change occurring between chromatic colors in reaction with an analyte; and at least one or additional nanoparticles mixed with the first metallic nanoparticles, wherein the color of the one or additional metallic nanoparticle is complementary to the first metallic nanoparticles, wherein the mixture forms an achromatic colorimetric sensor.

The achromatic colorimetric sensor may be arrayed. However, the present disclosure is not limited thereto. The achromatic colorimetric sensor may be arranged in various forms.

The detection of present achromatic colorimetric sensor using nanoparticles is accomplished by the color change occurring from achromatic colorimetric sensor in the presence of target analyte.

The first metallic nanoparticles may be rendered to have a specific color due to their strong surface plasmon absorption. The behavior of metallic nanoparticles may be sensitive to surroundings, and thus, the color of nanoparticles thereof may be changed to a different color. This color change of metallic nanoparticles may be observed with human naked eye.

The color of the added nanoparticles is complementary to the color of the first metallic nanoparticles. In this connection, the added nanoparticles may be single or plural depending on the color of the metallic nanoparticles. For example, the color of additional nanoparticles can be red when the color of the first metallic nanoparticles is bluish green. Alternatively, the colors of two added nanoparticles can be yellow and blue, when the color of the first metallic nanoparticles is red. Thus, the mixture of additional nanoparticles and the first metallic nanoparticles may render an achromatic color.

Further, amphiphilic polymers may be coated on the surfaces of the nanoparticles to prevent the nanoparticles being aggregated when exposed to an analyte or a specific environment. When one nanoparticle exists in a certain environment, for example, in a media with a high ionic concentration, the surface of the nanoparticles may be neutralized and thus become aggregated. This aggregation may cause a color change of nanoparticles. If the color of added nanoparticles changes when they are exposed to a certain environment, it may be unclear whether the overall color change of the achromatic colorimetric sensor is due to the color change of the first nanoparticles due to reaction with analyte or the color change of added nanoparticles. Thus, additional nanoparticles may be prevented from unwanted aggregation and resulting color change by increasing its stability via coating the surface of nanoparticles with amphiphilic polymer. A few examples of the amphiphilic polymer may include PVP or PEG. In this way, it may be determined that overall color change of the achromatic colorimetric sensor is resulted only from the color change occurring from the first metallic nanoparticles in the presence of analyte. Thus, when the achromatic colorimetric sensor is exposed to an analyte, its overall color change from an achromatic color to a chromatic color is due to the color change the first metallic nanoparticles via its interaction with analyte. Thus, the presence or absence of the analyte may be detected easily with the naked eye of the human.

FIG. 2A shows color-transition and change of UV-visible spectrum when gold nano-stars (AuNS) are employed as the first metallic nanoparticles. The gold nano-stars may exhibit a bluish green in ultra-pure water. The gold nano-stars may become colorless when reacting with a solution (for example, 1×PBS, etc.) by interacting with high concentrations of cationic targets. The gold nano-stars may exhibit a maximum absorption (bluish green) in about a 671 nm wavelength range, but have reduced extinction (become colorless) due to aggregation of gold nano-stars in a solution with high concentrations of cationic targets.

Figure 2B:
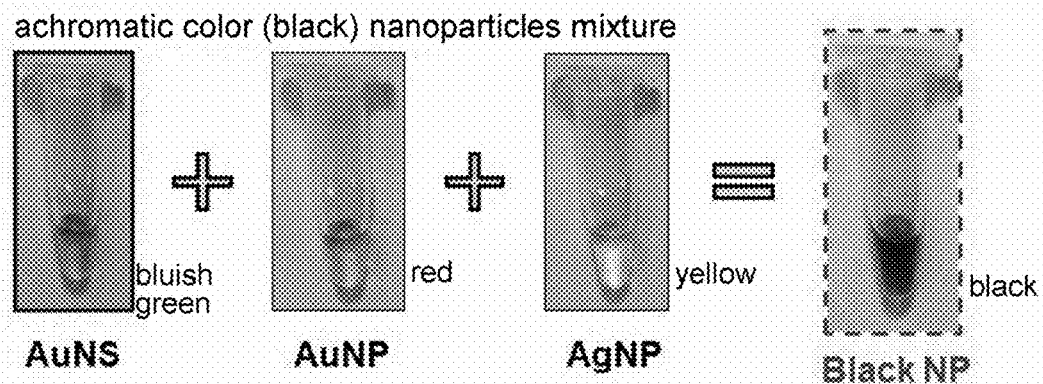
FIG. 2B shows a process of mixing gold nano-stars with complementary colored nanoparticles to render the gold nano-stars into an achromatic color (black), according to an embodiment.

FIG. 2B shows a process of mixing gold nano-stars with additional nanoparticles to render an achromatic colorimetric sensor with achromatic color (black). In an example, in order to render an achromatic colorimetric sensor with achromatic color (black), the gold nano-stars exhibiting a bluish green may be mixed with gold nanoparticles (AuNP) exhibiting red and silver nanoparticles (AgNP) exhibiting yellow in a volume ratio 2:1:1. This may lead to the achromatic colorimetric sensor exhibiting black color.

The gold nanoparticles with sizes of 7 to 20 nm may have the maximum absorption wavelength at about a 520 nm wavelength range yielding a red color. The gold nanoparticles may have citrate ions capped on their surface to exhibit a negative charge. Thus, the gold nanoparticles may repel against each other and thus may remain stable. However, when the gold nanoparticles are immersed in the solution of high concentration of ions, the surface of the gold nanoparticles may be neutralized due to cations in the solution. This neutralization may lead to an unwanted aggregation of the gold nanoparticles and thus, the color of the gold nanoparticles may change from red to a dark blue or violet. In the present disclosure, in order to suppress unwanted aggregation and thus unwanted color change of the gold nanoparticles (or any additional nanoparticles) whose color is complementary to the color of the first nanoparticles or gold nano-stars, the gold nanoparticles (or additional nanoparticles) may have amphiphilic polymers coated thereon.

The silver nanoparticles with sizes of 20 to 40 nm may have the maximum absorption wavelength at about a 417 nm wavelength range to yield a yellow color. When the silver nanoparticles are immersed in the solution of high concentration of ions, the surface of the sliver nanoparticles may be neutralized due to the cations in the solution. This neutralization may lead to an aggregation of the sliver nanoparticles and thus, the color of the sliver nanoparticles may change from yellow to a different color. In the present disclosure, in order to suppress unwanted aggregation and thus unwanted color change of the sliver nanoparticles (or any additional nanoparticles) whose color is complementary to the color of the first nanoparticles or gold nano-stars, the silver nanoparticles (or additional nanoparticles) may have amphiphilic polymers coated thereon.

Once again, as gold nano-stars, gold nanoparticles, and sliver nanoparticles are mixed with each other in a volume ratio of 2:1:1, the mixture may absorb all light in the visible region, 400 to 800 nm, and thus exhibit an achromatic black color. In this case, when the mixture is exposed to the analyte, only the gold nano-stars should have color change (from a bluish-green to colorless) with minimal color change from both gold nanoparticles and sliver nanoparticles. For this, as described above, in an example, an amphiphilic polymer, PVP, may be coated on the gold nanoparticles and sliver nanoparticles.

Figure 3:
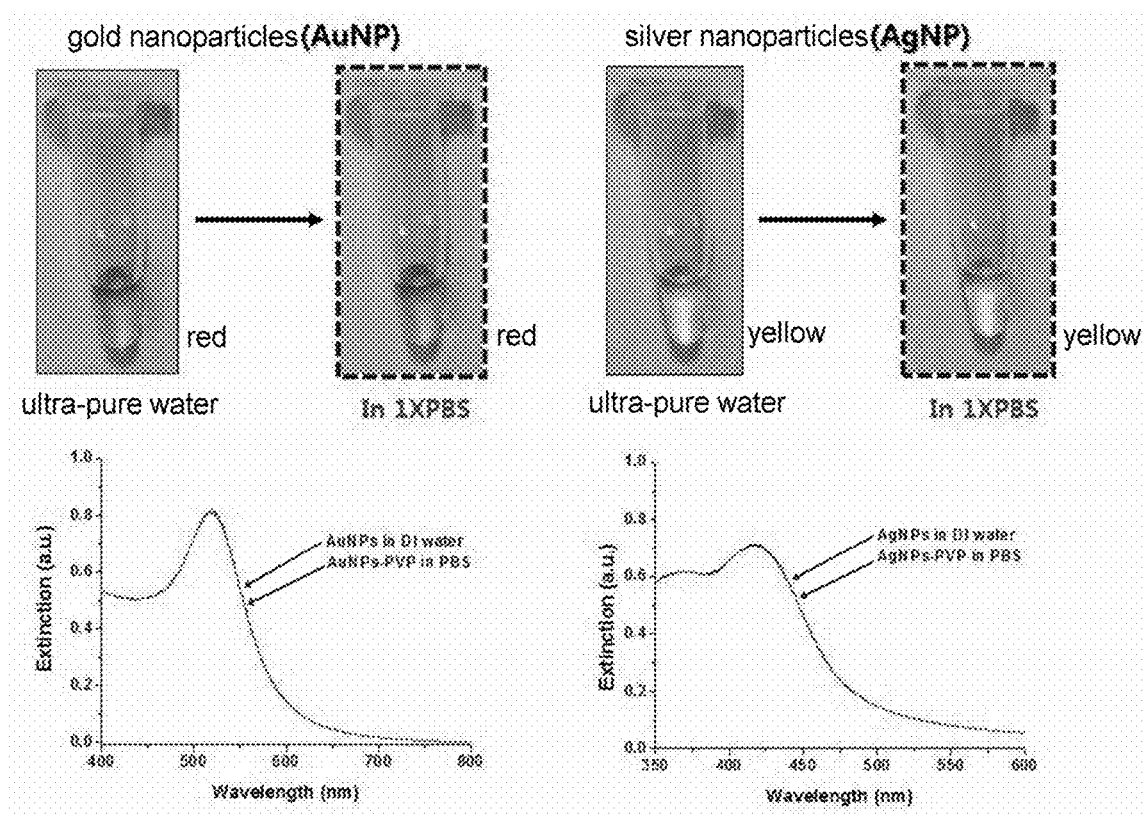
FIG. 3 shows negligible color change and the change of UV-vis spectrum when PVP-passivated nanoparticles are exposed to an analyte, according to an embodiment.

FIG. 3 shows a color change and UV-vis spectra when PVP-passivated nanoparticles are exposed to an analyte. As shown in FIG. 3, when the PVP-passivated nanoparticles are exposed to the analyte (for example, 1×PBS), the PVP-passivated nanoparticles may have no color change and may have the same UV-vis spectra as that when immersed in the ionized water (DI water). In this way, the gold nanoparticles and silver nanoparticles may have no color change when exposed to the analyte.

Figure 4:
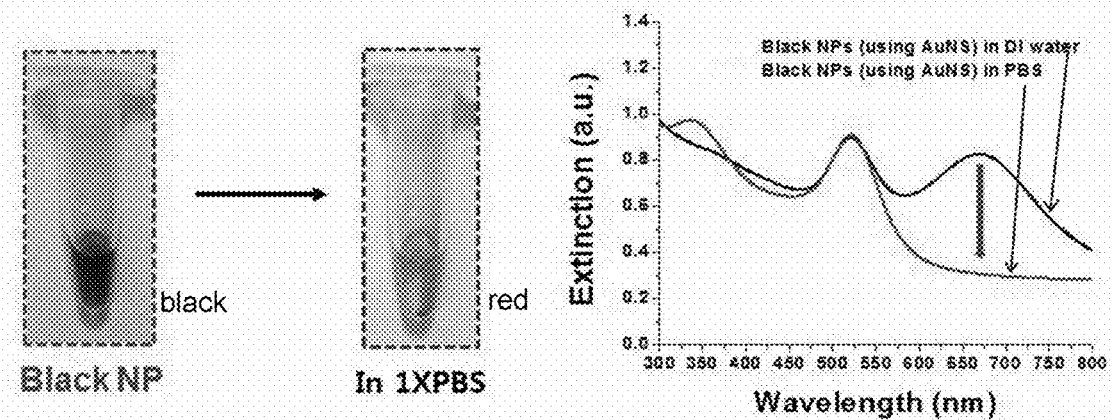
FIG. 4 shows data to identify the color change of an achromatic colorimetric sensor when the achromatic colorimetric sensor produced in accordance with an embodiment of the present disclosure is exposed to an analyte, according to an embodiment.

FIG. 4 shows data to identify color change of an achromatic colorimetric sensor when an achromatic colorimetric sensor produced in accordance with an embodiment of the present disclosure is exposed to an analyte. As shown in FIG. 4, the achromatic colorimetric sensor renders an achromatic black color. When the achromatic colorimetric sensor reacts with the analyte (1×PBS), both gold nanoparticles and silver nanoparticles may have no color change, exhibiting red and yellow, respectively, due to the treatment of amphiphilic polymer on the nanoparticle surface. However, the color of gold nano-stars may change from a bluish-green to colorless. In this way, overall color of an achromatic colorimetric sensor may change from black to orange. This color change of the sensor allows easy detection of analyte with naked eye. As shown from the absorption spectra, the achromatic colorimetric nanosensor may absorb all light in the visible region, 400 to 800 nm, in ultra-pure water. However, only absorption peaks of the gold nanoparticles and silver nanoparticles may be observed when achromatic colorimetric sensor is immersed in the 1×PBS solution.

Figure 5:
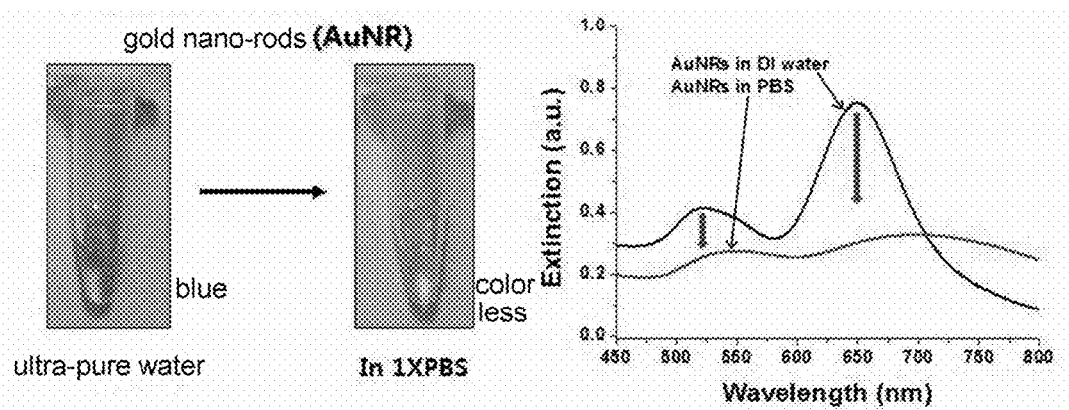
FIG. 5 shows color-transition and peak intensity change when gold nano-rods (AuNR) are used as a conventional colorimetric sensor, according to an embodiment.

FIG. 5 shows color-transition and UV-vis spectra when gold nano-rods (AuNR) are used as the first metallic nanoparticles. As shown in FIG. 5, the gold nano-rods (AuNR) may render blue color in ultra-pure water. When the gold nano-rods (AuNR) are immersed in the solution (for example, 1×PBS) with high concentrations of cationic analyte, the gold nano-rods (AuNR) may become colorless. As shown from the absorption spectrum, the gold nano-rods (AuNR) may have a maximum absorption in about 650 nm wavelength range (blue color). However, the gold nano-rods (AuNR) may have reduced peak intensity in the solution containing analytes (for example, 1×PBS) as AuNRs become aggregation and colorless.

Figure 6:
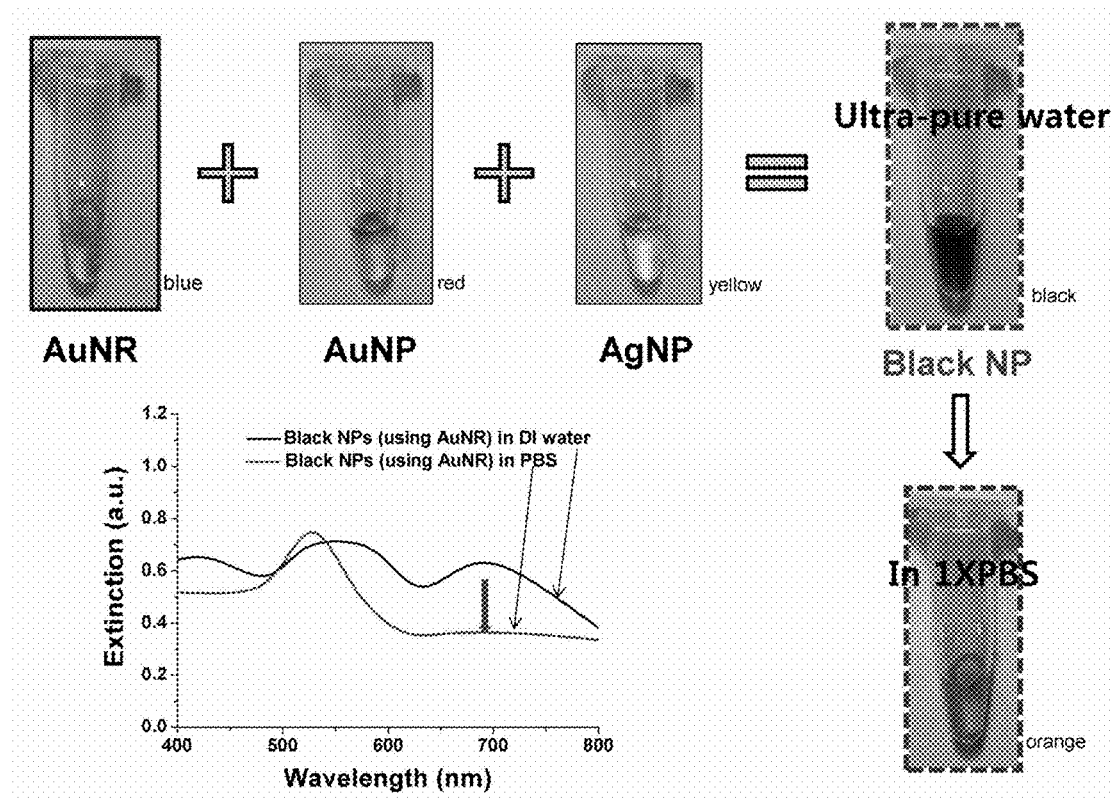
FIG. 6 shows a process of mixing gold nano-rods with complementary colored nanoparticles to render black colored achromatic colorimetric sensor and data to identify color change of the achromatic colorimetric sensor when it is exposed to an analyte, according to an embodiment.

FIG. 6 shows a process of mixing gold nano-rods with nanoparticles to render gold nano-rods into an achromatic colorimetric sensor (black) and data to identify the color change of an achromatic colorimetric sensor when it is exposed to an analyte. As shown in FIG. 6, gold nano-rods: gold nanoparticles: silver nanoparticles are mixed with each other in a volume ratio 2:1:2. Thus, the mixture renders a black colored achromatic colorimetric sensor.

The gold nanoparticles with sizes of 7 to 20 nm may have the maximum absorption wavelength at about a 520 nm wavelength range yielding red color. The gold nanoparticles may have citrate ions capped on their surface to exhibit a negative charge. Thus, the gold nanoparticles may repel against each other and thus may remain stable. However, when the gold nanoparticles are immersed in the solution of high concentration of ions, the surface of the gold nanoparticles may be neutralized due to cations in the solution. This neutralization may lead to an unwanted aggregation of the gold nanoparticles and thus, the color of the gold nanoparticles may change from red to dark blue or violet. In the present disclosure, in order to suppress unwanted aggregation and thus unwanted color change of the gold nanoparticles (or any additional nanoparticles) whose color is complementary to the color of the first nanoparticles or gold nano-rods, the gold nanoparticles (or any additional nanoparticles) may have amphiphilic polymers coated thereon.

The silver nanoparticles with sizes of 20 to 40 nm may have the maximum absorption wavelength at about a 417 nm wavelength range to yield yellow color. When the silver nanoparticles are immersed in the solution of high concentration of ions, the surface of the sliver nanoparticles may be neutralized due to the cations in the solution. This neutralization may lead to the aggregation of the sliver nanoparticles and thus, the color of the sliver nanoparticles may change from yellow to a different color. In the present disclosure, in order to suppress unwanted aggregation and thus unwanted color change of the sliver nanoparticles (or any additional nanoparticles) whose color is complementary to the color of the first nanoparticles or gold nano-rods, the silver nanoparticles (or additional nanoparticles) may have amphiphilic polymers coated thereon.

Thus, the mixture may absorb all light in the visible region, 400 to 800 nm, and thus exhibit an achromatic black color. In this case, when the mixture is exposed to the analyte, only the gold nano-stars should have color change (from bluish-green to colorless) with minimal color change from both gold nanoparticles and sliver nanoparticles. For this, as described above, in an example, an amphiphilic polymer, PVP, may be coated on the gold nanoparticles and sliver nanoparticles.

When the an achromatic colorimetric sensor reacts with the analyte (1×PBS), both gold nanoparticles and silver nanoparticles may have no color change, that is, exhibiting red and yellow, respectively, due to the amphiphilic polymer treatment on the nanoparticle surface. However, the color of gold nano-stars may change from bluish-green to colorless. In this way, overall color of an achromatic colorimetric sensor may change from black to orange. This color change of the sensor allows easy detection of analyte with naked eyes. As shown from the absorption spectra, the achromatic colorimetric nanosensor may absorb all light in the visible region, 400 to 800 nm, in the ultra-pure water. However, only absorption peaks of the gold nanoparticles and silver nanoparticles may be observed when achromatic colorimetric sensor is immersed in the 1×PBS solution.

Further, the metallic nanoparticles, that is, the first nanoparticles may have chemical or biological molecules bonded thereon. The chemical or biological molecule may have an activity. The attachment of various chemical or biological molecule on the nanoparticle surface may allow the present sensor to have various applications. To prove that the chemical or biological molecules are active, FIG. 7 and FIG. 8 may be referenced.

The chemical or biological molecules may be selected from a group consisting of DNA, RNA, aptamer, peptide, protein, antigen, antibody, chelator, etc.

Figure 7:
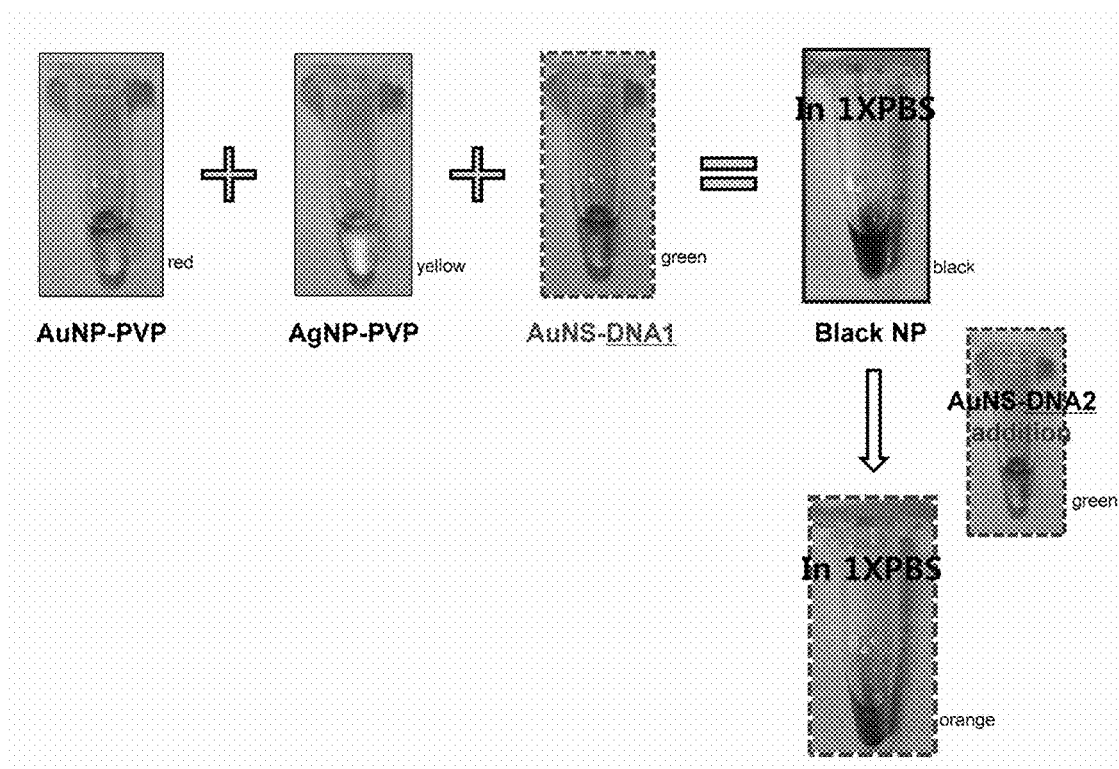
FIG. 7 shows an analysis result of an achromatic colorimetric sensor where biological molecules, DNA1 and DNA2, are bonded to gold nano-stars, according to an embodiment.

FIG. 7 shows an analysis result of an achromatic colorimetric sensor where biological molecules, DNA1 and DNA2, are bonded to gold nano-stars. As shown in FIG. 7, biological molecules DNA1 are bonded to the surface of the gold nano-stars (first surface modification: AuNS-DNA1). The AuNS-DNA1 is mixed with PVP-passivated gold nanoparticles and silver nanoparticles. This mixture renders an achromatic black color. Then, biological molecules DNA2 are bonded to the surface of the gold nano-stars (second surface modification: AuNS-DNA2). When the AuNS-DNA2 is added into the achromatic colored nanoparticles mixture, the DNA1 and DNA2 may be mutually bonded to each other, resulting in the aggregation of the gold nano-stars. In this way, the color of the sensor may change from black to orange.

Figure 8:
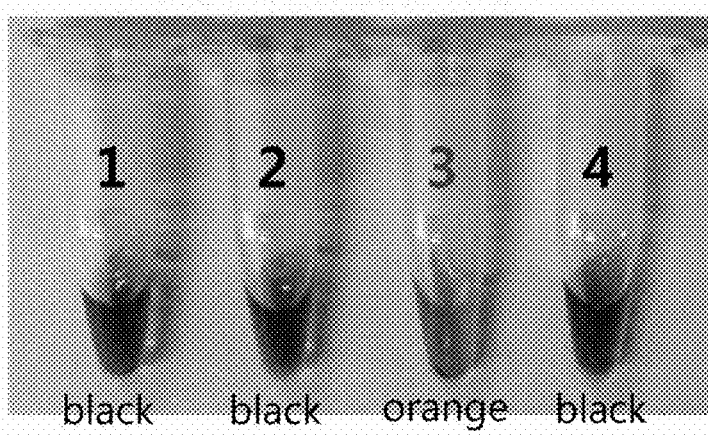
FIG. 8 shows analysis results of an achromatic colorimetric sensor where biological molecules are bonded to gold nano-stars, according to an embodiment.

FIG. 8 shows analysis results of an achromatic colorimetric sensor where biological molecules are bonded to gold nano-stars. In this embodiment, biological molecule DNA1 (SEQ ID NO: 1) is bonded to the surface of the gold nano-stars (first surface modification: AuNS-DNA1) to prepare the AuNS-DNA1 (first example). Separately, biological molecule DNA2 (SEQ ID NO: 2), which is complementary to DNA1, is bonded to the surface of the gold nano-stars (second surface modification: AuNS-DNA2) to prepare the AuNS-DNA2 (second example). PVP-capped gold nanoparticles and silver nanoparticles are both mixed with AuNS-DNA1 and AuNS-DNA2 to form the first example of black nanoparticles and the second example of black nanoparticles respectively. In the third example, the first example of black nanoparticles and the second example of black nanoparticles are mixed. In this third example, the mixture of the first example of black nanoparticles and the second example of black nanoparticles may become orange. As shown in the fourth example, once the mixture of the first example of black nanoparticles and the second example of black nanoparticles is heated, the sensor turns black again as DNA1 and DNA2 attached on the AuNS surface become dehybridized.

This color change may have happened due to the aggregation of the gold nano-stars caused by the biological interaction occurring between two complementary strands DNA1 and DNA2 attached on the surface of gold nano-stars. This color change of achromatic colorimetric sensor, occurring from an achromatic color to a chromatic color, can be used to detect various target analytes. As demonstrated from the present disclosure, the achromatic colorimetric sensor may be used for many applications including a chemical sensor, biological sensor, biomolecule sensor, etc.

Up to now, the achromatic colorimetric nanosensor using nanoparticles has been described. Hereinafter, an achromatic colorimetric nanosensor system for multiplexed detection using nanoparticles will be described in details.

The present achromatic colorimetric nanosensor for multiplexed detection using nanoparticles may include a mixture of at least two nanoparticles to render an achromatic color based on a subtractive mixing. Each of at least two nanoparticles may have chemical or biological molecules coated thereon. Thus, when the chemical or biological molecule attached on nanoparticle surface reacts with an analyte, a color-transition occurs from the mixture of nanoparticles. The detection can be accomplished by monitoring the color change from an achromatic to chromatic colors.

As used herein, the term "subtractive mixing" may refer to a color mixing method where the color of a resultant mixture has lower brightness than those of original colors. Especially, the subtractive mixing may be employed to render an achromatic color.

The analyte sensor may include at least two nanoparticles. Each of nanoparticles may have chemical or biological molecules attached thereto. The chemical or biological molecule may have a chemical or biological activity. The attachment of various chemical or biological molecules may allow the present sensor to be used for various applications. The chemical or biological molecules may be selected from a group consisting of DNA, RNA, aptamer, peptide, protein, antigen, antibody, chelator, etc. Since the chemical or biological molecules are active, the chemical or biological molecules may react with a target analyte. As each of metallic nanoparticles are functionalized with different chemical or biological molecules, the aggregation of different metallic nanoparticles can be caused by the presence of different target analyte. This aggregation of different metallic nanoparticles may exhibit various color changes of the sensor.

In other words, the achromatic colorimetric sensor of the present disclosure may be composed of plural nanoparticles. Each nanoparticle may have a corresponding active chemical or biological molecule attached thereto. When the corresponding active chemical or biological molecule attached on each nanoparticle reacts with a corresponding analyte, the color of achromatic colorimetric sensor of the present disclosure may have a color change. Thus, the number of the color changes may depend on the number of the nanoparticles used to make an achromatic colorimetric sensor. Thus, various analytes may be detected.

For example, each of the two nanoparticles used to make an achromatic colorimetric sensor may have a corresponding chemical or biological molecule coated thereon. When chemical or biological molecules coated on the surface of each nanoparticle react with corresponding analytes, respectively, the color-transition of the mixture of the two nanoparticles may occur to three colors. Thus, detection of analytes at three different conditions is possible.

Further, in the achromatic colorimetric sensor of the present disclosure, the mixture of the nanoparticles based on the subtractive mixing method renders an achromatic color which turns into a chromatic color in reaction with an analyte. The color change between an achromatic color and a chromatic color may allow an easy perception of the color change by a human naked eye.

The achromatic colorimetric sensor of the present disclosure may have applications including a chemical sensor, biological sensor, and biomolecule sensor.

Hereinafter, various color changes corresponding to combinations of metallic nanoparticles will be described.

In another embodiment of the present disclosure, a nanoparticle-based achromatic colorimetric sensor with the multi-detection may include a mixture of gold nano-particles, silver nano-particles, and gold nano-rods, wherein the mixture originally renders a black color. The gold nanoparticles (first nanoparticle), silver nano-particles (second nanoparticle), and gold nano-rods (third nanoparticle) may have first, second, third chemical or biological molecules coated thereon respectively. When the chemical or biological molecules react with the analytes, the achromatic colorimetric sensor may have color changes respectively.

The achromatic colorimetric sensor originally rendering black color may be produced via the mixture of gold nanoparticles (AuNP) rendering red, silver nanoparticles (AgNP) rendering yellow, and gold nano-rods (AuNR) rendering bluish-green color based on the subtractive RYB (Red-Yellow-Blue) color model. In this connection, the chemical or biological molecules are attached to the AuNPs, AgNPs, and AuNRs considering the stability and applications of the nanoparticles.

In this example, when the chemical or biological molecules coated on the metallic nanoparticles react corresponding analytes respectively, the color of achromatic colorimetric sensor may change to six different colors. Thus, detection of analytes at six different conditions is possible.

Hereinafter, a specific example may be representative of the above embodiment, however, embodiments are not limited thereto.

Figure 9A:
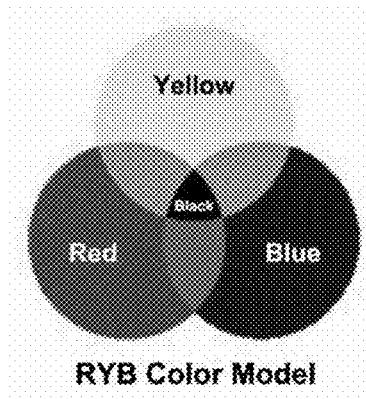
FIG. 9A shows an example of a color mixture based on a subtractive mixing method, according to an embodiment.

In this example, in order produce a black colored achromatic colorimetric sensor, gold nanoparticles (AuNP), silver nanoparticles (AgNP), and gold nano-rods (AuNR) are mixed using the subtractive mixing method. This may be confirmed with reference to FIG. 9A.

Further, the first (gold nanoparticles), second (silver nanoparticles), and third (gold nano-rods) nanoparticles may be designed to have DNA 1', DNA 2' and DNA 3' coated thereon which are specific to target DNAs (DNA1, DNA2, DNA3) respectively.

Figure 9B:
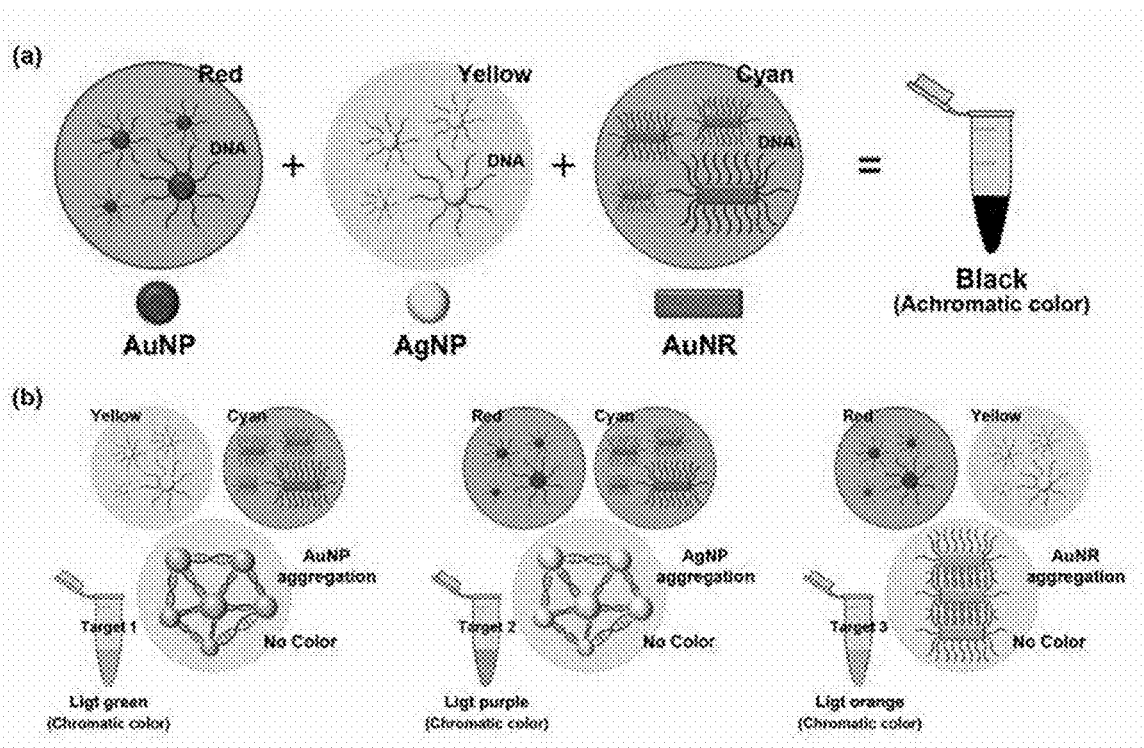
FIG. 9B shows an example of color transition of an achromatic colorimetric nanosensor which is produced by the mixture of metallic nanoparticles using a subtractive mixing method, according to an embodiment.

FIG. 9B shows an example of the color transition of an achromatic colorimetric sensor which is produced by mixing of three different metallic nanoparticles using a subtractive mixing method. When a target analyte DNA1 is present, only the first nanoparticles (gold nanoparticles) in the achromatic colorimetric sensor react with the DNA1 and thus aggregate. Thus, in a suitable concentration of DNA1, the first nanoparticles may change from red to colorless. Thus, the color of achromatic colorimetric sensor may change from black (achromatic color) to yellow green (chromatic color). Further, when a target DNA2 is present, only the second nanoparticles (silver nanoparticles) in the achromatic colorimetric sensor react with the DNA2 and thus aggregate. Thus, in a suitable concentration of DNA2, the second nanoparticles may change from yellow to colorless. Thus, the color of achromatic colorimetric sensor may change from black (achromatic color) to a purple color (chromatic color). Further, when a target DNA3 is present, only the third nanoparticles (gold nano-rods) in the achromatic colorimetric sensor react with the DNA3 and thus aggregate. Thus, in a suitable concentration of DNA3, the third nanoparticles may change from bluish-green to colorless. Thus, the color of achromatic colorimetric sensor may change from black (achromatic color) to an orange color (chromatic color).

Figure 10A:
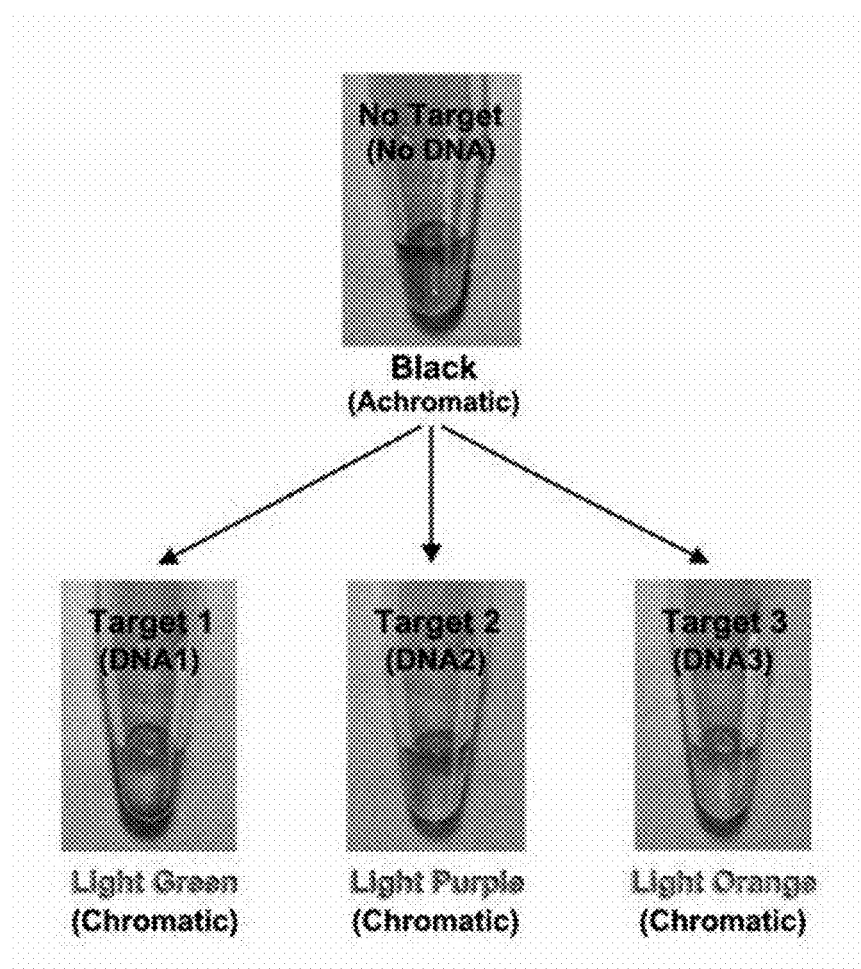
FIG. 10A and FIG. 10B show an embodiment where multi-detection is available using an achromatic colorimetric sensor with nanoparticles, according to an embodiment.
Figure 10B:
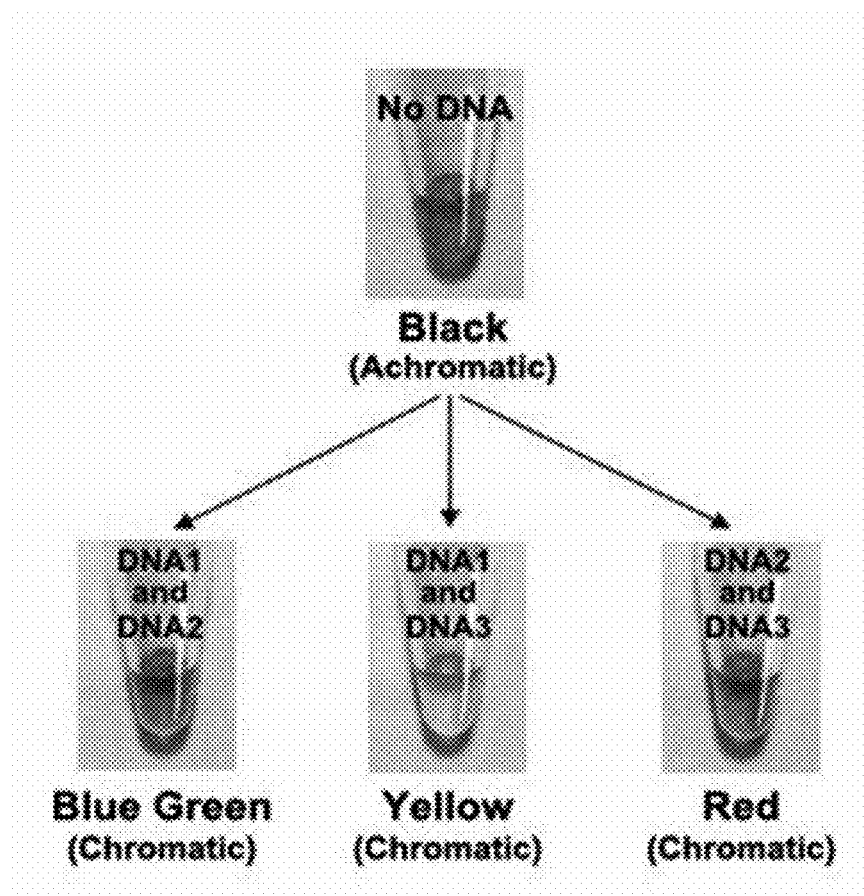

Further, when two types of analytes, for example DNA1 and DNA2, are present concurrently, the gold nanoparticles and silver nanoparticles may aggregate concurrently. In this way, the color of achromatic colorimetric sensor may change from black to a chromatic bluish-green. Further, when the DNA2 and DNA3 are present concurrently, the gold nano-rods and silver nanoparticles may aggregate concurrently. In this way, the color of achromatic colorimetric sensor may change from black to a chromatic red. Further, when the DNA1 and DNA3 are present concurrently, the gold nano-rods and gold nanoparticles may aggregate concurrently. In this way, the color of achromatic colorimetric sensor may change from black to a chromatic yellow. Such color changes are shown as FIG. 10A and FIG. 10B.

This achromatic colorimetric sensor system for multiplexed detection can be used for various analytes, depending on the types of biological or chemical molecules coated on the nanoparticles.

Figure 11:
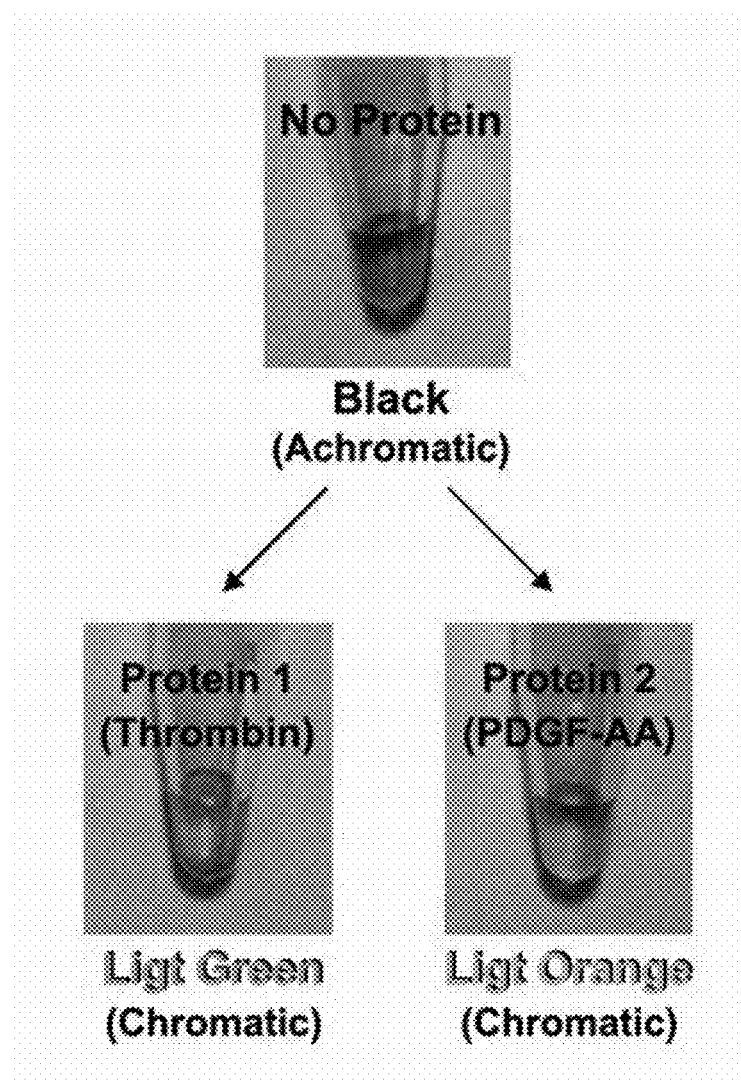
FIG. 11 show another embodiment where multiplexed detection is available using an achromatic colorimetric sensor with nanoparticles, according to an embodiment.

In the present disclosure, in order to prove the multi-detection, by way of example, the gold nanoparticles and gold nano-rods were coated with aptamers specific for thrombin and PDGF-AA, respectively. This example is shown in FIG. 11. FIG. 11 show another embodiment where multi-detection is possible using an achromatic colorimetric nanosensor in accordance with an embodiment of the present disclosure.

In this connection, various proteins may be detected concurrently in a single sensor system in a specific biological media, for example, serum, plasma, blood, etc. When thrombin is present in the plasma, gold nanoparticles may aggregate. Thus, the achromatic colorimetric sensor changes from black (achromatic color) to yellow green (chromatic color). Further, when PDGF-AA is present in the plasma, gold nano-rods may aggregate. Thus, the achromatic colorimetric sensor changes from the black (achromatic color) to orange (chromatic color).

As shown above, in this aspect of the present disclosure, the achromatic colorimetric sensor system for multiplexed detection may detect at least three analytes at the same time as its achromatic black color changes to at least three different chromatic colors in the presence of multiple analytes. This is different from a conventional nanoparticles-based colorimetric sensor system which uses a single nanoparticle to detect a single analyte. The present achromatic colorimetric sensor system for multiplexed detection may be used to build biological sensor or chemical sensor platforms where not only a single cell or molecule but also multiple cells or molecules may be detected concurrently in a one stop manner.

Reference throughout this specification to "in an example," "an embodiment," or similar language means that a particular feature, structure, or characteristic that is described in connection with the embodiment is included in at least one embodiment of the present disclosure. Thus, appearances of the phrases "in an example," "in an embodiment," and similar language throughout this specification may, but do not necessarily, all refer to the same embodiment.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An achromatic colorimetric sensor for multiplexed detection comprising:
a first nanoparticle exhibiting a first chromatic color;
a second nanoparticle exhibiting a second chromatic color;
a mixture of at least the first and second nanoparticles, the mixture exhibiting an achromatic color based on subtractive mixing; and
a chemical or biological molecule attached to each of the nanoparticles,
wherein when said chemical or biological molecules react with a corresponding analyte, the mixture changes color from the achromatic color to a chromatic color.

2. The sensor of claim 1, wherein reactions of the chemical or biological molecules attached to at least two nanoparticles enable at least three color changes of the achromatic colorimetric sensor.

3. The sensor of claim 1, wherein the analyte sensor includes a chemical sensor, a biological sensor, or a biomolecule sensor.

4. The sensor of claim 1, wherein the chemical or biological molecule has an activity.

5. The sensor of claim 1, wherein the chemical or biological molecule is selected from a group consisting of DNA, RNA, aptamer, peptide, protein, antigen, antibody, and chelator.

6. The sensor of claim 1, wherein the achromatic color is black.

7. A colorimetric sensor for multiplex detection comprising:
a first nanoparticle having a first chemically or biologically active molecule attached to a surface of the first nanoparticle, the first nanoparticle exhibiting a first chromatic color;
a second nanoparticle having a second chemically or biologically active molecule attached to a surface of the second nanoparticle, the second nanoparticle exhibiting a second chromatic color;
wherein the first nanoparticle and the second nanoparticle are in a mixture,
the mixture configured to display an achromatic color in solution prior to contact with one or more analytes,
the mixture configured to display a first color upon binding of one or more analytes to only the first chemically or biologically active molecule,
the mixture configured to display a second color upon binding of one or more analytes to only the second chemically or biologically active molecule, and
the mixture configured to display a third color upon simultaneous binding of one or more analytes to only both the first chemically or biologically active molecule and the second chemically or biologically active molecule.

8. The colorimetric sensor of claim 7 further comprising:
a third nanoparticle having a third chemically or biologically active molecule attached to a surface of the third nanoparticle, the third nanoparticle exhibiting a third chromatic color,
wherein the mixture comprises the first nanoparticle, the second nanoparticle, and the third nanoparticle,
the mixture configured to display a fourth color upon binding of one or more analytes to only the third chemically or biologically active molecule,
the mixture configured to display a fifth color upon simultaneous binding of one or more analytes to only both the first chemically or biologically active molecule and the third chemically or biologically active molecule, and
the mixture configured to display a sixth color upon simultaneous binding of one or more analytes to only both the second chemically or biologically active molecule and the third chemically or biologically active molecule.

9. The sensor of claim 7, wherein the achromatic color is black.

10. The sensor of claim 8, wherein the achromatic color is black.

* * * * *